United States Patent
Hagen et al.

(10) Patent No.: US 6,858,624 B2
(45) Date of Patent: Feb. 22, 2005

(54) ARYL FUSED AZAPOLYCYCLIC COMPOUNDS

(75) Inventors: Anne E. Hagen, Ledyard, CT (US); R. Scott Obach, Gales Ferry, CT (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 34 days.

(21) Appl. No.: 10/306,500

(22) Filed: Nov. 27, 2002

(65) Prior Publication Data

US 2003/0166582 A1 Sep. 4, 2003

Related U.S. Application Data

(60) Provisional application No. 60/334,502, filed on Nov. 30, 2001.

(51) Int. Cl.[7] ........................ A61K 31/495; A61K 31/50; C07D 221/22
(52) U.S. Cl. ........................ 514/307; 514/13; 514/183; 514/227.8; 514/255.03; 514/285; 514/561; 536/17.4; 536/18.7; 558/286; 540/476; 540/479; 540/482; 544/284; 544/353; 546/97
(58) Field of Search ........................ 514/307, 13, 183, 514/227.8, 255.01, 285, 561, 300, 43; 536/17.4, 18.7; 558/286; 540/476, 479, 482; 544/284, 353; 546/97

(56) References Cited

U.S. PATENT DOCUMENTS 5,663,377 A * 9/1997 Curley et al. ............... 549/417
5,977,131 A 11/1999 Nagel
6,020,335 A 2/2000 Nagel et al.
6,605,610 B1 * 8/2003 Coe et al. .................. 514/250

FOREIGN PATENT DOCUMENTS

| EP | 0955301 | 3/1999 |
|---|---|---|
| WO | WO 9818798 | 5/1998 |
| WO | WO 9935131 | 7/1999 |
| WO | WO 9955680 | 11/1999 |
| WO | WO 0162736 | 8/2001 |

* cited by examiner

*Primary Examiner*—James O. Wilson
*Assistant Examiner*—Devesh Khare
(74) *Attorney, Agent, or Firm*—Scully, Scott, Murphy & Presser

(57) ABSTRACT

This invention is directed to compounds of the formula (I):

(I)

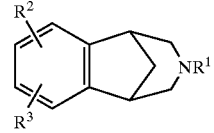

and their pharmaceutically acceptable salts, wherein $R^1$, $R^2$, and $R^3$ are as defined herein; intermediates for the synthesis of such compounds, pharmaceutical compositions containing such compounds; and methods of using such compounds in the treatment of nicotine addiction/withdrawal and CNS disorders.

9 Claims, No Drawings

ARYL FUSED AZAPOLYCYCLIC COMPOUNDS

CROSS-REFERENCE TO RELATED APPLICATIONS

This application claims priority to U.S. Provisional Patent Application Ser. No. 60/334,502, filed Nov. 30, 2001.

BACKGROUND OF THE INVENTION

This invention relates to aryl fused azapolycyclic compounds, as defined more specifically by formula I below. Compounds of formula I bind to neuronal nicotinic acetylcholine specific receptor sites and are useful in modulating cholinergic function. Such compounds are useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (eq., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

The compounds of this invention may also be used in combination with an antidepressant such as, for example, a tricyclic antidepressant or a serotonin reuptake inhibiting antidepressant (SRI), in order to treat both the cognitive decline and depression associated with AD, PD, stroke, Huntington's chorea or traumatic brain injury (TBI); in combination with muscarinic agonists in order to stimulate both central muscarinic and nicotinic receptors for the treatment, for example, of ALS, cognitive dysfunction, age-related cognitive decline, AD, PD, stroke, Huntington's chorea and TBI; in combination with neurotrophic factors such as NGF in order to maximize cholinergic enhancement for the treatment, for example, of ALS, cognitive dysfunction, age-related cognitive decline, AD, PD stroke, Huntington's chorea and TBI; or in combination with agents that slow or arrest AD such as cognition enhancers, amyloid aggregation inhibitors, secretase inhibitors, tau kinase inhibitors, neuronal anti-inflammatory agents and estrogen-like therapy.

Other compounds that bind to neuronal nicotinic receptor sites are referred to in U.S. patent application Ser. No. 08/963,852, which was filed on Nov. 4, 1997. The foregoing application is owned in common with the present application, and is incorporated herein by reference in its entirety. In particular, a number of compounds which bind to neuronal nicotinic receptor sites and are useful in modulating cholinergic function are referred to in International Patent Publication No. WO 01/62736, filed Feb. 8, 2001; International Patent Publication No. WO 99/35131, filed Nov. 13, 1998; International Patent Publication No. WO 99/55680, filed Apr. 8, 1999; International Patent Publication No. WO 98/18798, filed Oct. 15, 1997; U.S. Pat. No. 5,977,131, filed Mar. 31, 1998; U.S. Pat. No. 6,020,335, filed Nov. 4, 1997; and European Patent Publication No. EP 0 955 301 A2, filed Mar. 25, 1999. The foregoing applications, owned in common with the present application and incorporated herein by reference in their entirety.

SUMMARY OF THE INVENTION

This invention relates to aryl fused azapolycyclic compounds of the formula (I)

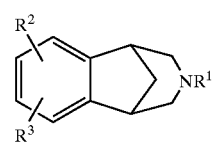

$R^1$ is independently hydrogen or —COOR$^4$, wherein $R^4$ is a group of formula

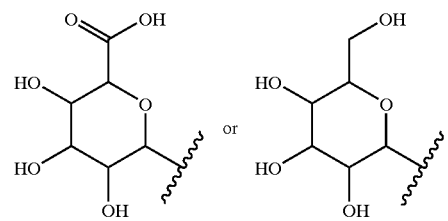

$R^2$ and $R^3$, together with the benzo ring to which they are attached, form a bicyclic ring system selected from the following:

-continued

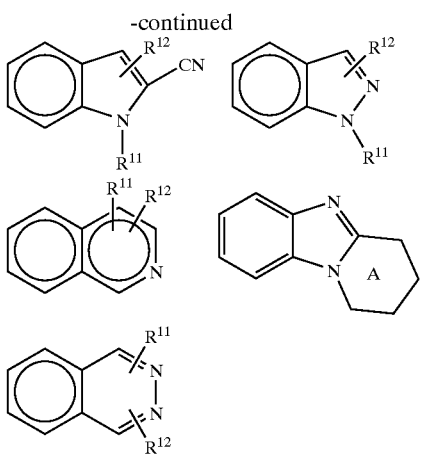

wherein one of the carbon atoms of ring A can optionally be replaced with oxygen or $N(C_1-C_6)$alkyl;

wherein $R^{11}$ and $R^{12}$ are selected, independently, from hydrogen, $(C_1-C_6)$alkyl; and $(C_1-C_6)$alkoxy-$(C_0-C_6)$alkyl- wherein the total number of carbon atoms does not exceed six and wherein any of the alkyl moieties may optionally be substituted with from one to seven fluorine atoms; nitro, cyano, halo, amino, $(C_1-C_6)$alkylamino-, $((C_1-C_6)alkyl)_2$amino-, $-CO_2R^5$, $-CONR^6R^7$, $-SO_2NR^8R^9$, $-C(=O)R^{10}$, $-XC(=O)R^{10}$, phenyl, monocyclic heteroaryl, or when attached to a nitrogen atom, a group of formula:

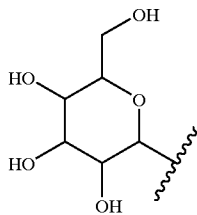

each $R^5$, $R^6$, $R^7$, $R^8$, $R^9$ and $R^{10}$ is selected, independently, from hydrogen and $(C_1-C_6)$alkyl, or $R^6$ and $R^7$, or $R^8$ and $R^9$ together with the nitrogen to which they are attached, form a pyrrolidine, piperidine, morpholine, azetidine, piperazine, $-N-(C_1-C_6)$ alkylpiperazine or thiomorpholine ring, or a thiomorpholine ring wherein the ring sulfur is replaced with a sulfoxide or sulfone; and each X is, independently, $(C_1-C_6)$alkylene;

with the proviso that when $R^1$ is H, then at least one of $R^{11}$ or $R^{12}$ must be a group of formula:

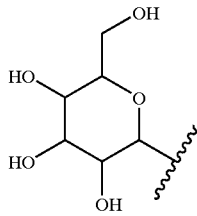

attached to a nitrogen atom in the ring formed by groups $R^2$ and $R^3$, and forming an ammonium ion center on that nitrogen atom if necessary to accommodate the existing bonding relationships; and pharmaceutically acceptable salts of such compounds.

Examples of possible heteroaryl groups within the definition of $R^2$ and $R^3$ are the following: thienyl, oxazoyl, isoxazolyl, pyridyl, pyrimidyl, thiazolyl, tetrazolyl, isothiazolyl, triazolyl, imidazolyl, tetrazolyl, pyrrolyl and the following groups:

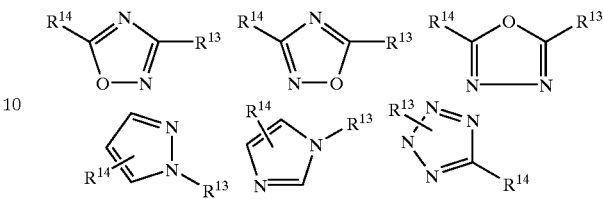

wherein one of $R^{13}$ and $R^{14}$ is hydrogen or $(C_1-C_6)$alkyl, and the other is a bond to the benzo ring of formula I.

Preferred embodiments of formula I are wherein $R^2$ and $R^3$, together with the benzo ring to which they are attached, form a bicyclic ring system selected from the following:

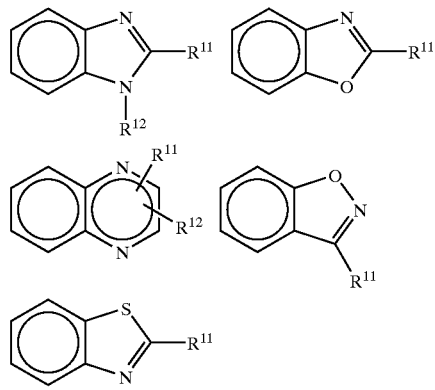

wherein $R^{11}$ and $R^{12}$ are as defined above.

More preferred embodiments of formula I are wherein $R^2$ and $R^3$, together with the benzo ring to which they are attached, form a group:

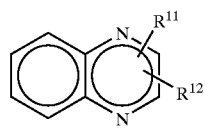

wherein $R^{11}$ and $R^{12}$ are as defined above.

The most preferred embodiments of formula I of the invention are selected from the group consisting of:

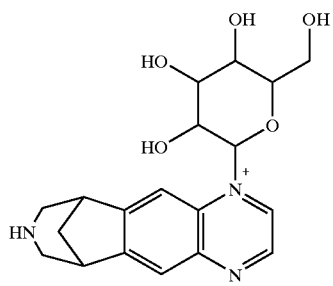

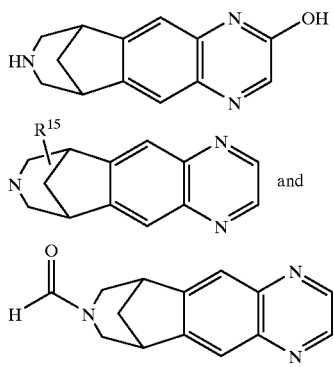

Other preferred compounds of the invention comprise:

wherein $R^{15}$ is an oxo group, which forms a carbonyl functional with any of the available carbon atoms on the unsaturated portion of the molecule.

Unless otherwise indicated, the term "halo", as used herein, includes fluoro, chloro, bromo and iodo.

Unless otherwise indicated, the term "alkyl", as used herein, includes straight chain moieties, and where the number of carbon atoms suffices, branched and cyclic moieties.

The term "alkoxy", as used herein, means "—O-alkyl" or "alkyl-O—", wherein "alkyl" is defined as above.

The term "alkylene", as used herein, means an alkyl radical having two available bonding sites (i.e., -alkyl-), wherein "alkyl" is defined as above.

Unless otherwise indicated, the term "one or more substituents", as used herein, refers to from one to the maximum number of substituents possible based on the number of available bonding sites.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. The invention includes all enantiomers, diastereomers, and other stereoisomers of such compounds of formula I, as well as racemic and other mixtures thereof.

The present invention also relates to all radiolabeled forms of the compounds of the formula I. Preferred radiolabeled compounds of formula I are those wherein the radiolabels are selected from as $^3H$, $^{11}C$, $^{14}C$, $^{18}F$, $^{123}I$ and $^{125}I$. Such radiolabeled compounds are useful as research and diagnostic tools in metabolism studies, such as pharmacokinetics studies, etc., and in binding assays in both animals and man.

The present invention also relates to a pharmaceutical composition for use in reducing nicotine addiction or aiding in the cessation or lessening of tobacco use in a mammal, including a human, comprising an amount of a compound of the formula I, or a pharmaceutically acceptable salt thereof, that is effective in reducing nicotine addiction or aiding in the cessation or lessening of tobacco use and a pharmaceutically acceptable carrier.

The present invention also relates to a method for reducing nicotine addiction or aiding in the cessation or lessening of tobacco use in a mammal, including a human, comprising administering to said mammal an amount of a compound of the formula I, or a pharmaceutically acceptable salt thereof, that is effective in reducing nicotine addiction or aiding in the cessation or lessening of tobacco use.

The present invention also relates to a method of treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.q., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.q., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising an amount of a compound of the formula I, or a pharmaceutically acceptable salt thereof, and a pharmaceutically acceptable carrier.

This invention also relates to the pharmaceutically acceptable acid addition salts of the compounds of formula I.

Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malic acid, di-p-toluoyl tartaric acid, and mandelic acid, as well salts formed from other acids known to those of skill in the art to form pharmaceutically acceptable acid addition salts to basic compounds. Other possible acid addition salts are, e.g., salts containing pharmaceutically acceptable anions, such as the hydroiodide, nitrate, sulfate or bisulfate, phosphate or acid phosphate, acetate, lactate, gluconate, saccharate, benzoate, methanesulfonate, ethanesulfonate, benzenesulfonate, and pamoate (i.e., 1.1'-methylene-bis-(2-hydroxy-3-naphthoate)salts).

DETAILED DESCRIPTION OF THE INVENTION

Except where otherwise stated, $R^1$ through $R^{15}$ and structural formula I in the reaction schemes and discussion that follow are defined as above. Methods of synthesizing arylfused azapolycyclic compound precursors are set forth in International Patent Publication No. WO 01/62736, filed Feb. 8, 2001; and International Patent Publication No. WO 99/35131, filed Nov. 13, 1998; incorporated herein by reference in their entirety.

A number of studies have been conducted on precursor compounds to those of formula I of the present invention. In particular, studies have been carried out on 5,8,14-triazatetracyclo[10.3.1.0$^{2,11}$0.0$^{4,9}$]-hexadeca-2(11),3,5,7,9-pentaene:

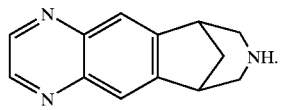

Means of the synthesis of this compound may be found International Patent Publication No. WO 99/35131 and WO 01/62736. In analyses of this particular precursor compound in liver microsomes, it was demonstrated that 5,8,14-triazatetracyclo[10.3.1.0$^{2,11}$0.0$^{4,9}$]-hexadeca-2(11),3,5,7,9-pentaene underwent N-carbamoyl glucuronidation to form an active compound of formula:

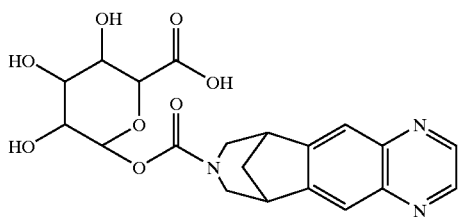

when specific conditions and cofactors were used to support this type of biotransformation reaction (bicarbonate buffer, $CO_2$ atmosphere, UDPGA).

The compound 5,8,14-triazatetracyclo[10.3.1.0$^{2,11}$0.0$^{4,9}$]-hexadeca-2(11),3,5,7,9-pentaene has also been studied in vivo (rat, monkey, mouse, and human). Metabolite structures are described in Scheme I below. Metabolites in human circulation included the N-carbamoyl glucuronide, N-formyl:

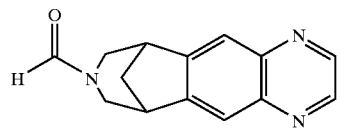

and N-hexose conjugates (at either or both the quinoxaline nitrogen position and the azabicyclic nitrogen position)

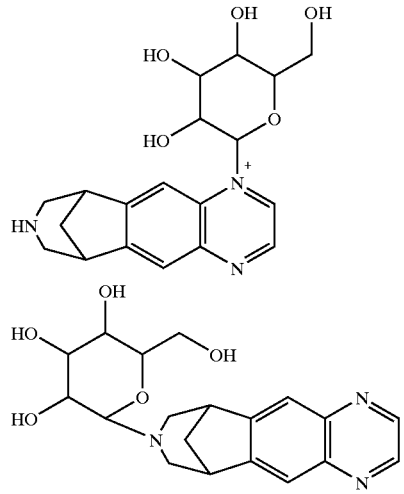

as well as a minor metabolite (assigned as a carbonyl metabolite as the molecular weight was 14 mass units greater than 5,8,14-triazatetracyclo[10.3.1.0$^{2,11}$0.0$^{4,9}$]-hexadeca-2(11),3,5,7,9-pentaene):

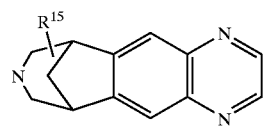

wherein $R^{15}$ is an oxo group, which forms a carbonyl functional with any of the available carbon atoms on the unsaturated portion of the molecule.

The N-carbamoyl glucuronide represents an unusual, albeit not unprecedented metabolite that arises via association of carbon dioxide with the secondary amine followed by glucuronidation. Preclinical species possessed these metabolites in addition to some minor putative oxidative metabolites. The only excreted metabolites in human were the hydroxyquinoxaline metabolite (2.9% of dose):

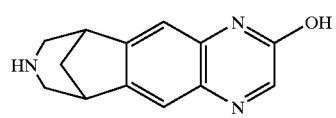

and N-carbamoyl glucuronide (3.6% of dose). The N-carbamoyl glucuronide was present in rat and monkey. The hydroxyquinoxaline metabolite was also shown to be present in rat urine.

SCHEME I

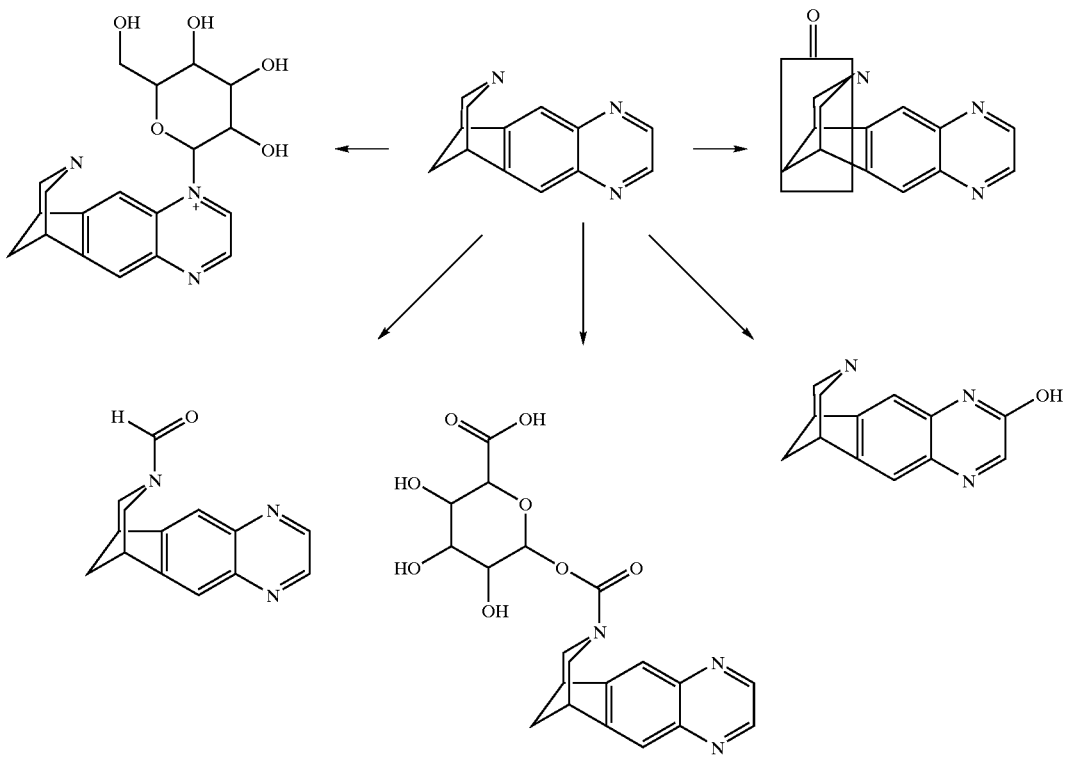

The compounds of the formula I and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically and this can be done by way of creams, a patch, jellies, gels, pastes, ointments and the like, in accordance with standard pharmaceutical practice.

Biological Assay

The effectiveness of the active compounds in suppressing nicotine binding to specific receptor sites is determined by the following procedure which is a modification of the methods of Lippiello, P. M. and Fernandes, K. G. (in *The Binding of L-[³H]Nicotine To A Single Class of High-Affinity Sites in Rat Brain Membranes, Molecular Pharm.*, 29, 448–54, (1986)) and Anderson, D. J. and Arneric, S. P. (in *Nicotinic Receptor Binding of ³H-Cytisine, ³H-Nicotine and ³H-Methylcarmbamylcholine In Rat Brain, European J. Pharm.*, 253, 261–67 (1994)).

Procedure

Male Sprague-Dawley rats (200–300 g) from Charles River were housed in groups in hanging stainless steel wire cages and were maintained on a 12 hour light/dark cycle (7 a.m.–7 p.m. light period). They received standard Purina Rat Chow and water ad libitum.

The rats were killed by decapitation. Brains were removed immediately following decapitation. Membranes were prepared from brain tissue according to the methods of Lippiello and Fernandez (*Molec Pharmacol*, 29, 448–454, (1986) with some modifications. Whole brains were removed, rinsed with ice-cold buffer, and homogenized at 0° in 10 volumes of buffer (w/v) using a Brinkmann Polytron™, setting 6, for 30 seconds. The buffer consisted of 50 mM Tris HCl at a pH of 7.5 at room temperature. The homogenate was sedimented by centrifugation (10 minutes; 50,000×g; 0 to 4° C. The supernatant was poured off and the membranes were gently resuspended with the Polytron and centrifuged again (10 minutes; 50,000×g; 0 to 4° C. After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM $MgCl_2$, 2 mM $CaCl_2$ and has a pH of 7.4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 μL of vehicle, blank, or test compound solution, respectively. To each tube was added 200 μL of [³H]-nicotine in assay buffer followed by 750 μL of the membrane suspension. The final concentration of nicotine in each tube was 0.9 nM. The final concentration of cytisine in the blank was 1 μM. The vehicle consisted of deionized water containing 30 μL of 1 N acetic acid per 50 mL of water. The test compounds and cytisine were dissolved in vehicle. Assays were initiated by vortexing after addition of the membrane suspension to the tube. The samples were incubated at 0 to 4° C. in an iced shaking water bath. Incubations were terminated by rapid filtration under vacuum through Whatman GF/B™ glass fiber filters using a Brandel™ multi-manifold tissue harvester. Following the initial filtration of the assay mixture, filters were washed two times with ice-cold assay buffer (5 m each). The filters were then placed in counting vials and mixed vigorously with 20 ml of Ready Safe™ (Beckman) before quantification of radioactivity. Samples were counted in a LKB Wallach Rackbeta™ liquid scintillation counter at 40–50% efficiency. All determinations were in triplicate.

Calculations

Specific binding (C) to the membrane is the difference between total binding in the samples containing vehicle only and membrane (A) and non-specific binding in the samples containing the membrane and cytisine (B), i.e., Specific binding=$(C)=(A)-(B)$.

Specific binding in the presence of the test compound (E) is the difference between the total binding in the presence of the test compound (D) and non-specific binding (B), i.e., $(E)=(D)-(B)$.

% Inhibition=$(1-((E)/(C))$times 100.

The compounds of the invention that were tested in the above assay exhibited $IC_{50}$ values of less than 10 μM.

What is claimed is:
1. A compound of the formula (I)

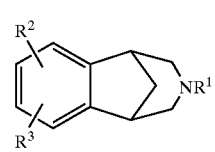

(I)

wherein $R^1$ is —$COOR^4$, wherein $R^4$ is a group of formula

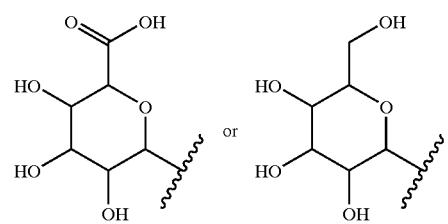

$R^2$ and $R^3$, together with the benzo ring to which they are attached, form a bicyclic ring system selected from the following:

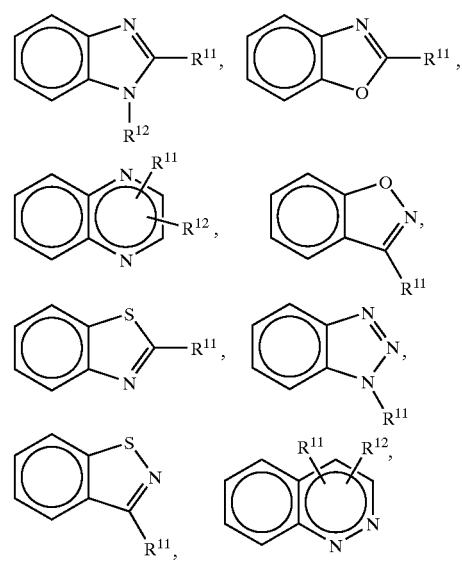

-continued

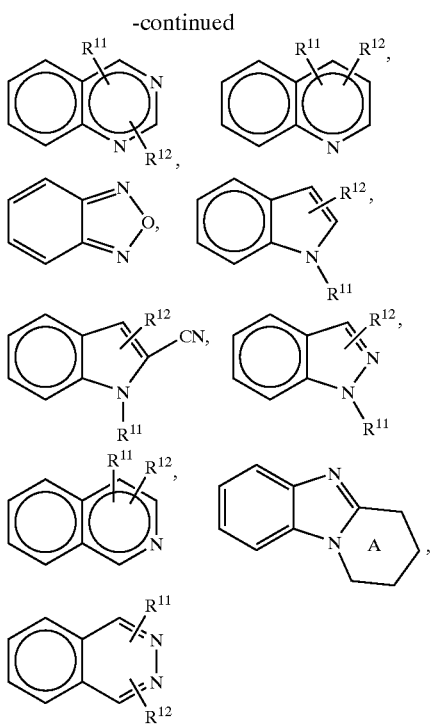

wherein one of the carbon atoms of ring A can optionally be replaced with oxygen or $N(C_1-C_6)$alkyl;

wherein $R^{11}$ and $R^{12}$ are selected, independently, from hydrogen, $(C_1-C_6)$alkyl; and $(C_1-C_6)$alkoxy-$(C_0-C_6)$alkyl- wherein the total number of carbon atoms does not exceed six and wherein any of the alkyl moieties may optionally be substituted with from one to seven fluorine atoms; nitro, cyano, halo, amino, $(C_1-C_6)$alkylamino-, $((C_1-C_6)$alkyl$)_2$amino-, —$CO_2R^5$, —$CONR^6R^7$, —$SO_2NR^8R^9$, —$C(=O)R^{10}$, —$XC(=O)R^{10}$, phenyl, monocyclic heteroaryl, or when attached to a nitrogen atom, a group of formula:

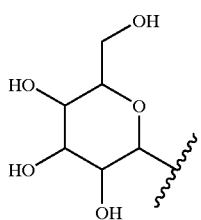

each $R^5$, $R^6$, $R^7$, $R^8$, $R^9$ and $R^{10}$ is selected, independently, from hydrogen and $(C_1-C_6)$alkyl, or $R^6$ and $R^7$, or $R^8$ and $R^9$ together with the nitrogen to which they are attached, form a pyrrolidine, piperidine, morpholine, azetidine, piperazine, —N—$(C_1-C_6)$alkylpiperazine or thiomorpholine ring, or a thiomorpholine ring wherein the ring sulfur is replaced with a sulfoxide or sulfone; and each X is, independently, $(C_1-C_6)$alkylene;

with the proviso that when $R^1$ is H, then at least one of $R^{11}$ or $R^{12}$ must be a group of formula:

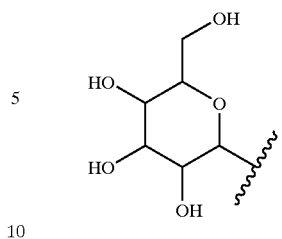

attached to a nitrogen atom in the ring formed by groups $R^2$ and $R^3$, and forming an ammonium ion center on that nitrogen atom if necessary to accommodate the existing bonding relationships; and pharmaceutically acceptable salts of such compounds.

2. A compound according to claim 1 wherein $R^2$ and $R^3$, together with the benzo ring to which they are attached, form a bicyclic ring system selected from the following:

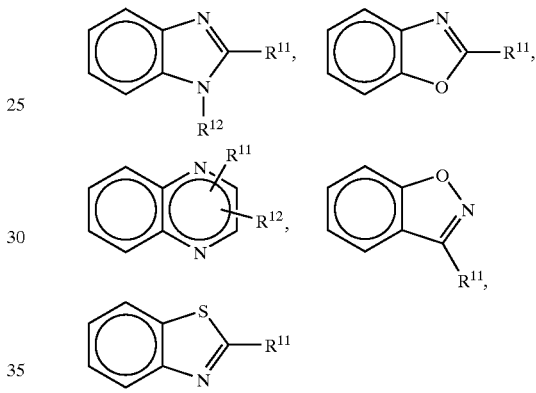

wherein $R^{11}$ and $R^{12}$ are as defined I claim 1.

3. A compound according to claim 1 wherein $R^2$ and $R^3$, together with the benzo ring to which they are attached, form a group:

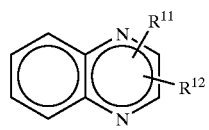

wherein $R^{11}$ and $R^{12}$ are as defined in claim 1.

4. A pharmaceutical composition comprising an amount of a compound according to claim 1, or a pharmaceutically acceptable salt thereof, and a pharmaceutically acceptable carrier.

5. A compound according to claim 1 selected from the group consisting of:

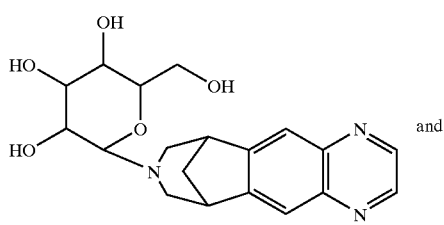

and

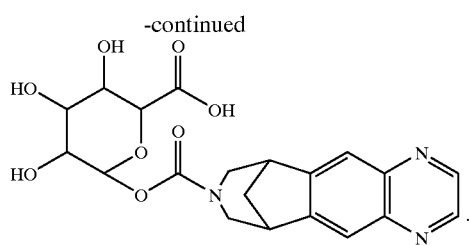

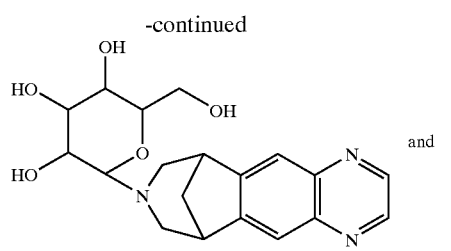

6. The compound according to claim 1, wherein said compound is in an isolated form.

7. The compound according to claim 5, wherein said compound is in an isolated form.

8. The compound according to claim 9, wherein said compound is in an isolated form.

9. A compound having the following formulae:

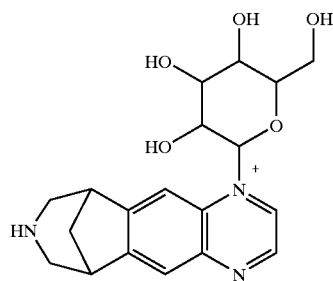

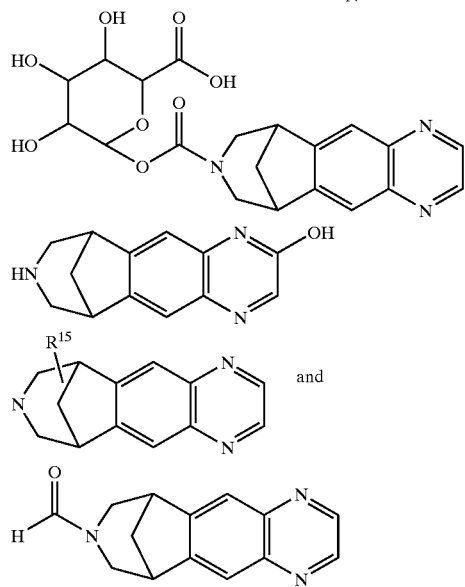

wherein $R^{15}$ is an oxo group, which forms a carbonyl functional with any of the available carbon atoms on the unsaturated portion of the molecule.

* * * * *